US00PP14164P29

(12) United States Plant Patent
Schlueter

(10) Patent No.: US PP14,164 P2
(45) Date of Patent: Sep. 23, 2003

(54) ***HIBISCUS ROSA-SINENSIS* PLANT NAMED 'SNOWFIRE'**

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/153,118

(22) Filed: May 22, 2002

(51) Int. Cl.[7] ..... A01H 5/00

(52) U.S. Cl. ..... Plt./257

(58) Field of Search ..... Plt./257

*Primary Examiner*—Kent Bell
(74) *Attorney, Agent, or Firm*—Christie, Parker & Hale, LLP

(57) ABSTRACT

A new variety of *Hibiscus rosa-sinensis* plant named 'Snowfire', characterized by a large multi-colored flower of red petals with irregular patches of white and orange and a dark maroon "eye". It is a free-flowering plant with an upright, compact habit. The foliage is glossy and dark green.

5 Drawing Sheets

BOTANICAL CLASSIFICATION/CULTIVAR DESIGNATION

*Hibiscus rosa-sinensis* cultivar 'Snowfire'.

BACKGROUND OF THE INVENTION

The present invention relates to a new and distinct variety of *Hibiscus rosa-sinensis*, which was developed in a controlled breeding program in Webster, Tex. by the originator Mr. Barry Schlueter. The varietal denomination of the new variety is 'Snowfire'.

The genus Hibiscus comprises about 250 species of herbs, shrubs and trees in warm temperate and tropical regions; with leaves usually simple, mostly palmately veined, lobed or parted; flowers mostly solitary in the leaf axils but sometimes in racemes, corymbs or panicles. Hibiscus is included in the family Malvaceae, which comprises about 95 genera of herbs, shrubs and trees originating in tropical and temperate regions. *Hibiscus rosa-sinensis* is a glabrate shrub, seldom over 8 feet tall in cultivation, but treelike to 15 feet or more in tropical regions. Leaves to 6 inches long, ovate, usually serrate, mostly glossy green. Flowers solitary in upper leaf axils.

The new Hibiscus is a product of a planned breeding program conducted by the inventor in Webster, Tex. The objective of the program was to create new Hibiscus selections with improved bloom quality, color and floriferousness, plants that can be commercially produced on their own root systems, and improved plant habit with regard to vigor and post-production longevity.

SUMMARY OF THE INVENTION

The new variety originated in a controlled breeding program from a cross between 'Al Schlueter' (unpatented) as the female, or seed, parent and 'Lady in Red' (unpatented) as the male, or pollen, parent. The cultivar 'Snowfire' was discovered and selected by the Inventor as a flowering plant within the progeny of the stated cross. 'Snowfire' differs from its parents and other known cultivars of *Hibiscus rosa-sinensis* by the following characteristics in combination:

1. Upright, compact symmetrical plant habit that is suitable for container production;

2. Shiny dark green leaves;
3. Vigorous growth habit;
4. Large unique multi-colored flowers with irregular patches of white and orange against red petals with a dark maroon "eye"; and
5. Free-flowering.

Asexual reproduction of the new variety by stem cuttings, performed in Webster, Tex. and Fulshear, Tex. have confirmed that the distinctive characteristics of the new variety are stable and transmitted to succeeding generations, and the new variety reproduces true to type.

COMPARISON WITH PARENTS AND OTHER VARIETIES

'Snowfire' is distinguished from its female parent 'Al Schlueter' (unpatented) by its flowing red blooms with random patches of white and orange with a dark maroon "eye"; 'Al Schlueter' bloom color is coppery brown. 'Snowfire' is distinguished from its male parent 'Lady in Red' (unpatented) by its improved flower color combinations and floriferousness; 'Lady in Red' has a dark red flower with irregular flower form.

Plants of 'Snowfire' can be compared to plants of the cultivar 'Wild Thing' (unpatented). However, in side-by-side comparisons conducted in Webster, Tex., plants of the new cultivar differ from plants of the cultivar 'Wild Thing' in the following characteristics:

1. Flowers of 'Snowfire' are brighter in color than flowers of 'Wild Thing';
2. Plants of 'Snowfire' are more vigorous than plants of the cultivar 'Wild Thing'; and
3. Plants of 'Snowfire' possess healthier foliage and a better growth habit than the cultivar 'Wild Thing'.

BRIEF DESCRIPTION OF ILLUSTRATIONS

The accompanying illustrations show a plant of the new cultivar in a photographic illustration as true to color as is reasonably possible to make in an illustration of this character.

DESCRIPTION OF THE NEW VARIETY

Figure 1:
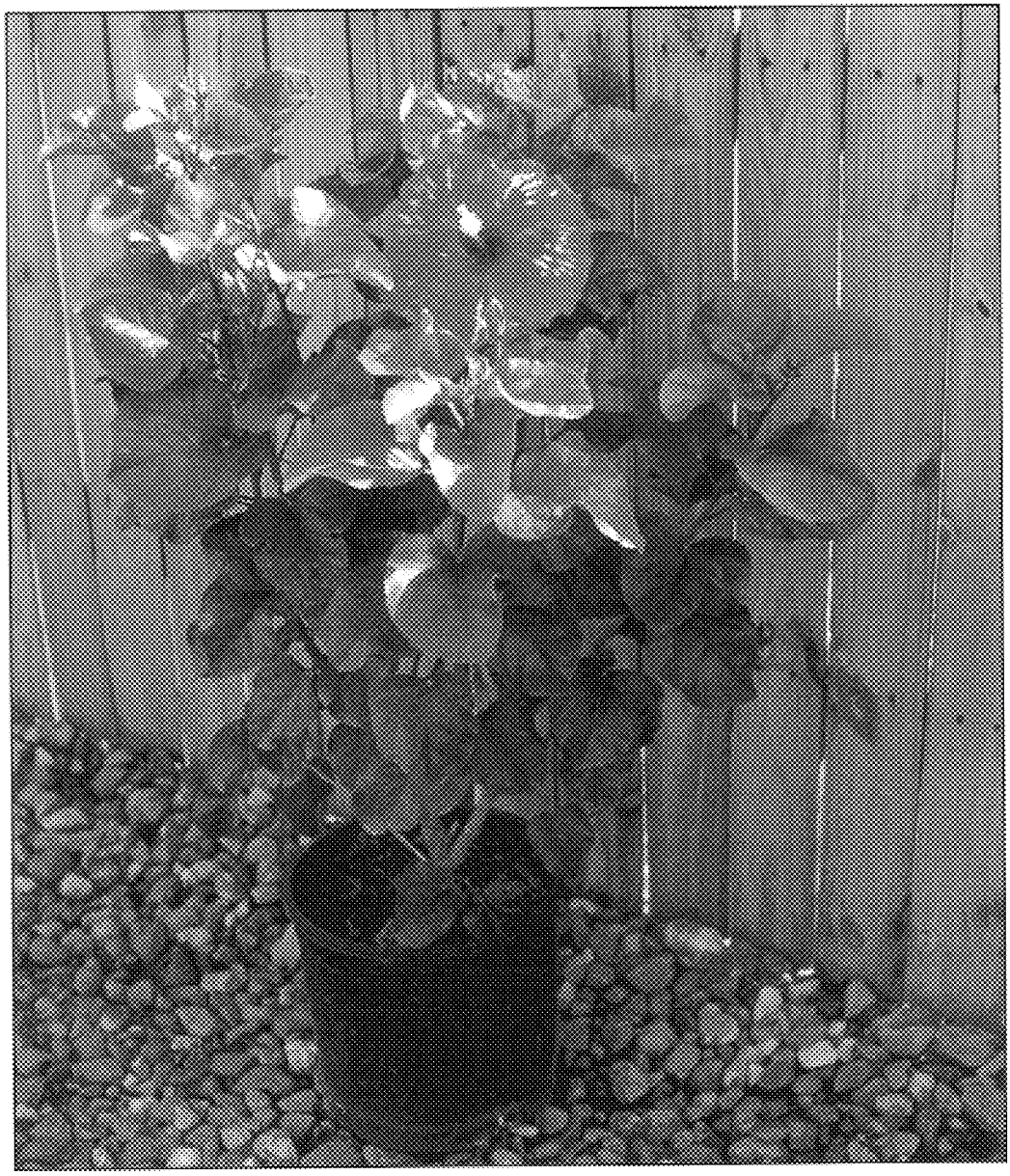
FIG. 1 illustrates a side perspective view of a typical plant of 'Snowfire'.
Figure 2:
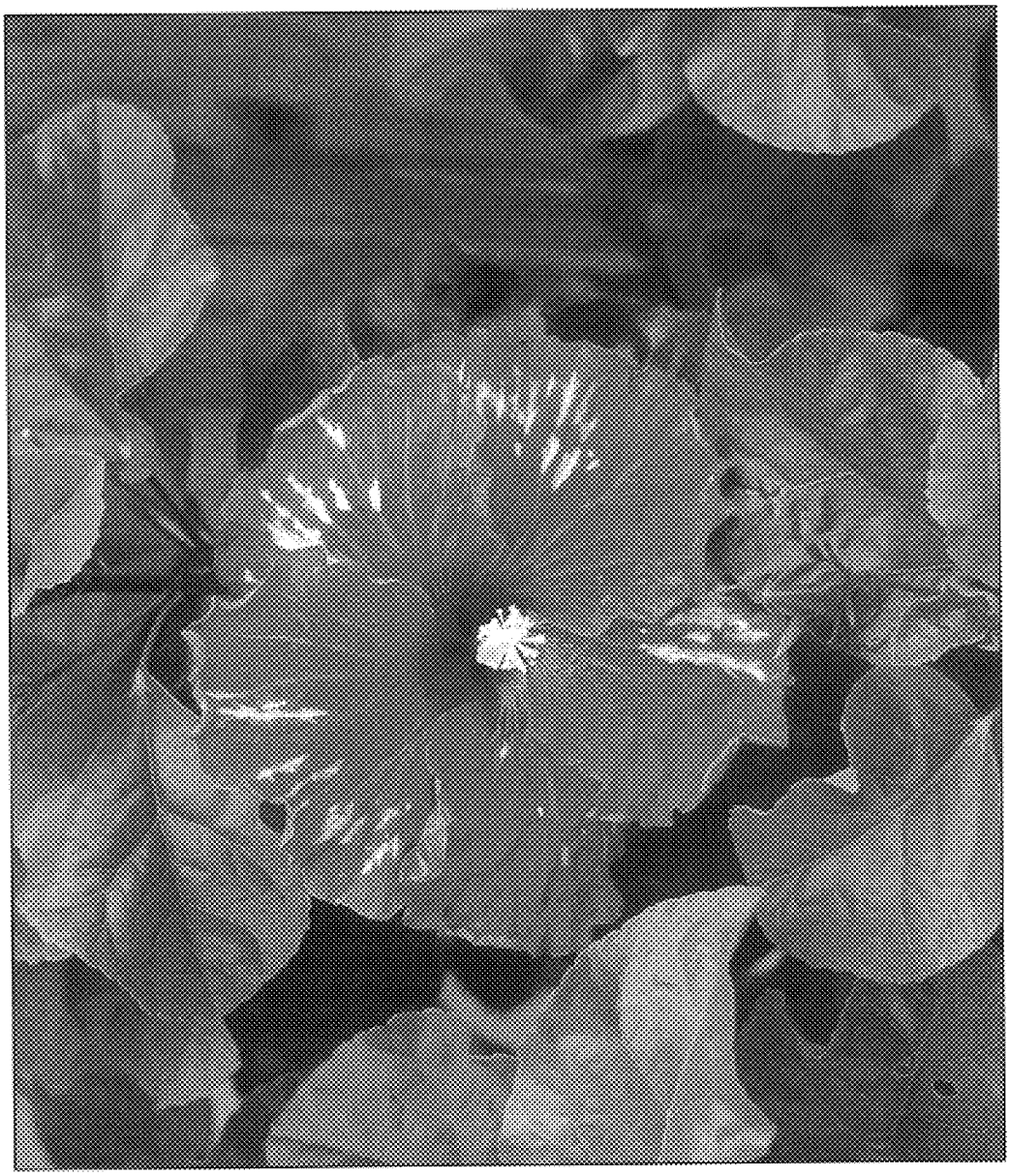
FIG. 2 illustrates a close-up view of a typical flower of 'Snowfire'.
Figure 3:
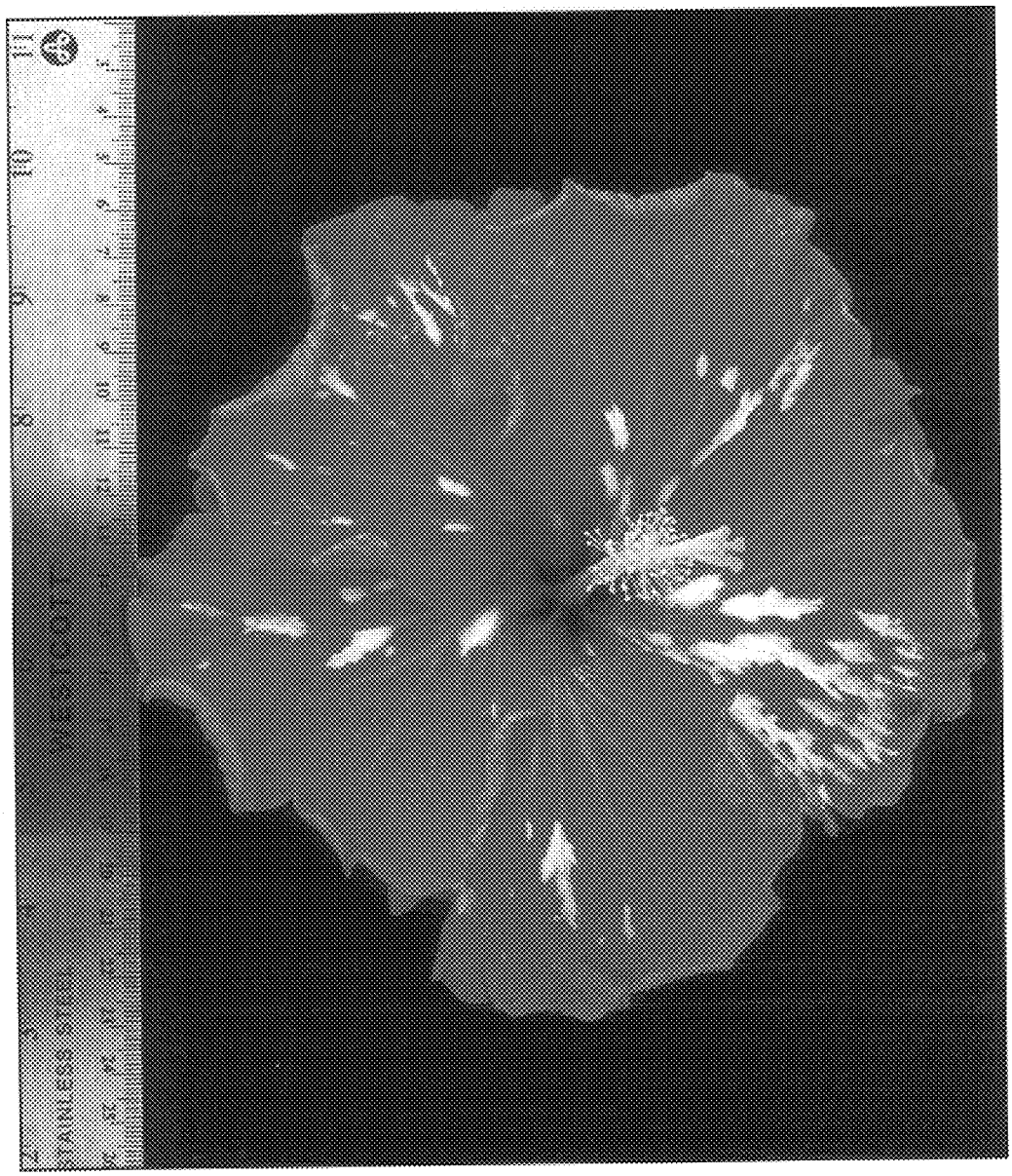
FIG. 3 illustrates the scale of a typical flower of 'Snowfire'.
Figure 4:
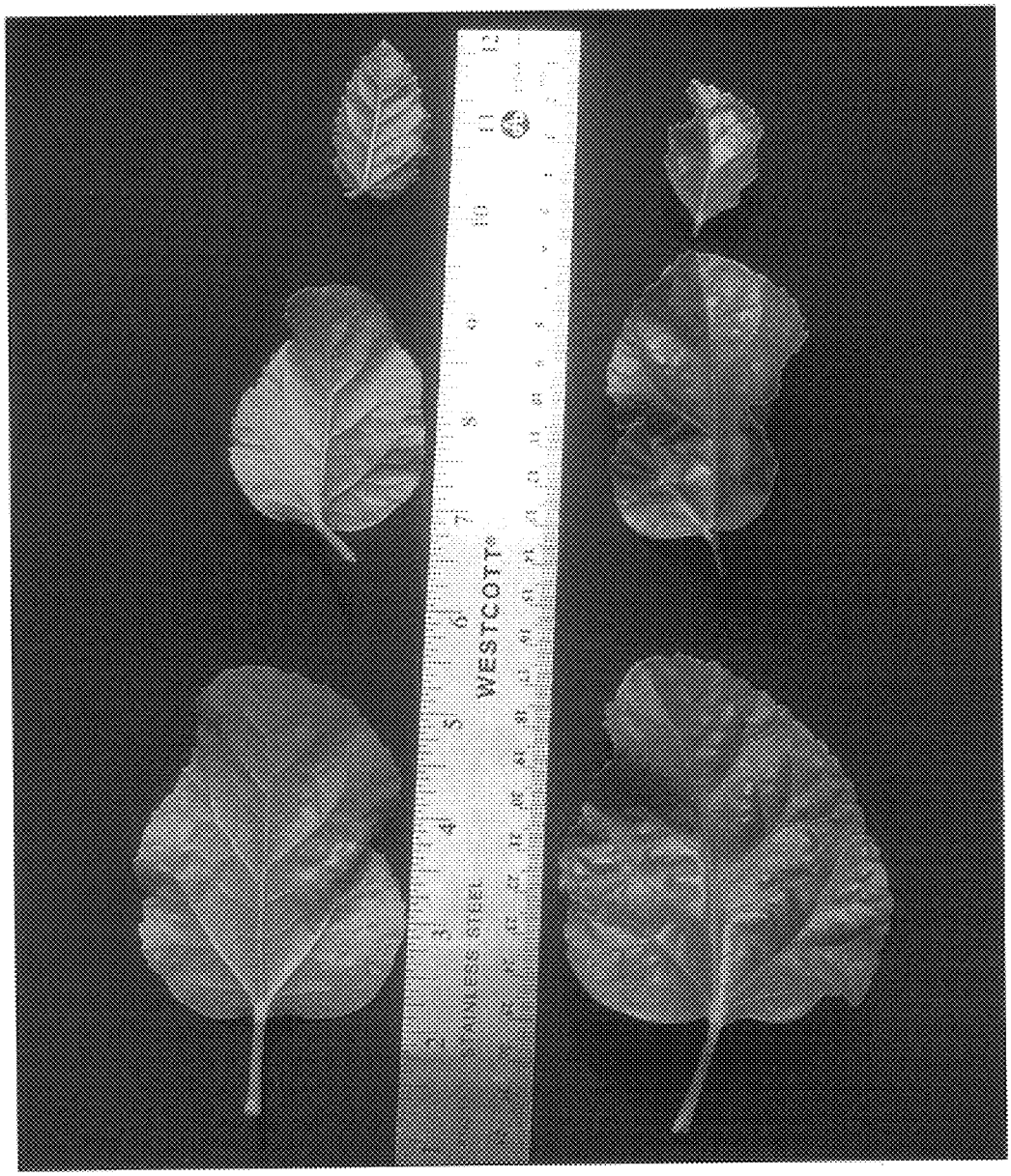
FIG. 4 illustrates the typical young to mature foliage of 'Snowfire'; the abaxial and adaxial surfaces are shown at each stage.
Figure 5:
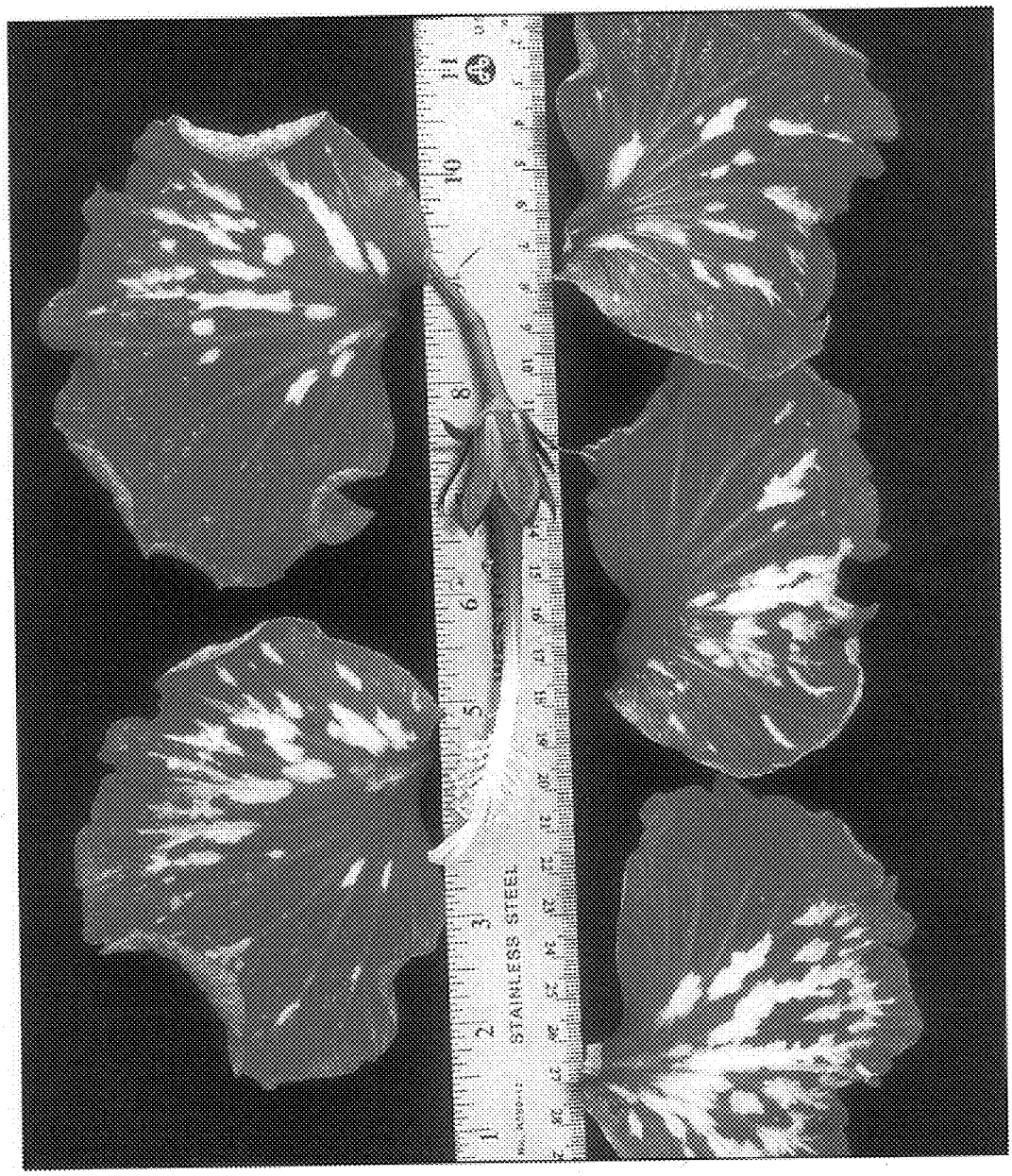
FIG. 5 illustrates a dissected flower of 'Snowfire', including shape and size of petals and characteristics of the reproductive structures.

'Snowfire' has not been observed under all possible environmental, cultural and light conditions. The following observations and descriptions are of plants grown in Fulshear, Tex., in August 2001, under polypropylene shadecloth providing a 30% light reduction, and under conditions which closely approximate commercial production. Plants described were approximately 1-year old and in a Number 3 nursery container.

In this description, color references are to The Royal Horticultural Society Colour Chart (1995) and terminology used in the color descriptions herein refers to plate numbers in this color chart. Phenotypic expression may vary with light intensity, cultural and environmental conditions.

CLASSIFICATION

Botanical: *Hibiscus rosa-sinensis* 'Snowfire'.

Parentage:

*Female.*—*Hibiscus rosa-sinensis* 'Al Schlueter' (unpatented).

*Male.*—*Hibiscus rosa-sinensis* 'Lady in Red' (unpatented).

Propagation: By stem cuttings.

Time to initiate rooting: Approximately 14 to 21 days at 21° to 24° C.

Time to develop roots: Approximately 42 to 56 days at 21° to 24° C.

Root description/habit: Fine to medium; fibrous; freely branching.

PLANT

Size:

*Height.*—Approximately 55 cm from soil level to top of flowers.

*Diameter/spread.*—Approximately 60 cm.

Form & growth habit: Perennial, evergreen shrub; mostly upright and somewhat spreading.

Branching: Freely branching; approximately 4 to 8 lateral branches develop after pinching.

*Lateral branches.*—Approximately 20 cm long and 5 mm in diameter; Immature color is near 146C to 146D, mature branches become woody and color is near 199C to 199D.

*Internode length.*—Approximately 4 cm.

LEAF

Shape: Cordate.

*Apex.*—Rounded.

*Base.*—Obtuse to slightly cordate.

Leaf size: Approximately 10 cm long and 10 cm wide.

Arrangement: Alternate, single; symmetrical.

Margin: Undulate with crenate margins.

Aspect: Undulate.

Texture/substance: Glabrous, shiny.

Coloration:

*Young foliage.*—Upper side: Near Yellow-Green Group 146A. Underside: Near Yellow-Green Group 146B.

*Mature foliage.*—Upper side: Near Green Group 147A. Underside: Near Green Group 146B.

Petioles:

*Size.*—Approximately 3 cm long, 3 mm across.

*Coloration.*—Near Green Group 137A.

*Texture.*—Smooth.

Hardiness: USDA Zone 10 (30° F. to 40° F.).

Pests/diseases: Resistance to known Hibiscus diseases had not been observed on plants grown under conditions approximating commercial practices.

INFLORESENCE

Bloom period: Typically year-round under subtropical and tropical conditions.

Flower arrangement: Arranged singly at terminal leaf axils; free-flowering with 3 to 4 flower buds and/or open flowers per terminal apex; flowers face upright and slightly outward.

Flower appearance: Rounded red petals with a dark maroon "eye" or center; the outer third of the petals have irregular patches of white and orange; flowers are open for about 1 day before closing; flowers persistent.

Flower size: Approximately 18 cm in diameter; with the flower set flat on a horizontal plane, the stigma and style are about 6.5–7.0 cm above the petal surface, the ruffling of the petals can vary between 1.5 and 3.0 cm above the petal surface.

Buds (just prior to showing color):

Rate of opening: Approximately 1 or 2 days, depending on temperature.

*Shape.*—Elliptic.

*Length.*—Approximately 3.7 cm.

*Diameter.*—Approximately 2 cm.

*Color.*—Near Green Group 137B.

Fragrance: None noted.

Petals:

*Number/arrangement.*—Corolla consists of 5 overlapping petals.

*Shape.*—Spatulate with rounded apex and cuneate base.

*Size.*—Approximately 10 cm long and 9.5 cm wide.

*Margin.*—Entire, but ruffled.

*Texture.*—Smooth.

Color:

*Upper surface.*—The "eye" or throat is near Greyed-Purple Group 187A; mid-petal is near Red Group 46B; margins near 42A; irregular patches near White Group 155B and others near Orange Group 24B and Orange-Red Group 30A.

*Lower suface.*—Mostly near Red Group 48B to 48C, with irregular patches near Yellow Group 10B; margins near Orange-Red Group 35A.

Sepals:

*Number/arrangement.*—5 sepals fused into a star-shaped calyx.

*Size.*—About 1.6 cm in length, about 4 mm in width.

*Shape.*—Linear with acuminate apices.

*Margin.*—Entire.

*Color.*—Upper surface, upper ⅔ is near 146B, lower ⅓ is near 146D and Lower surface is near 146B.

Peduncles:

*Length.*—Approximately 4 cm.

*Diameter.*—Approximately 2 mm.

*Angle.*—Upright to about 45°.
*Strength.*—Strong, flexible.
*Color.*—Near Yellow-Green Group 146B to 146C.

REPRODUCTIVE ORGANS

Androecium:
*Stamens.*—Numerous; about 52.
*Length.*—Approximately 4 mm.
*Filament color.*—Near Red Group 51A.
*Anther size.*—Approximately 1 mm in length.
*Pollen amount.*—Abundant.
*Pollen color.*—White Group 155B.

Gynoecium:
*Pistil number.*—One.
*Pistil length.*—6.5 cm.
*Stigma appearance.*—5; rounded.
*Stigma diameter.*—Approximately 2 mm.
*Stigma color.*—Near Orange-Red Group 32A.
*Style color.*—Lower third near Greyed-Purple Group 187B; mid-third near Red Group 50B; upper-third near White Group 155C.

Seed production: Seed production has not been observed.

I claim:

1. A new and distinct variety of *Hibiscus rosa-sinensis* plant named 'Snowfire', as illustrated and described herein.

* * * * *